(12) United States Patent
Crider, Jr. et al.

(10) Patent No.: US 10,959,621 B2
(45) Date of Patent: *Mar. 30, 2021

(54) LIVESTOCK HEALTH MONITORING SYSTEM AND METHOD OF USE

(71) Applicant: FEVERTAGS, LLC, Aramarillo, TX (US)

(72) Inventors: Richard Arelin Crider, Jr., Dripping Springs, TX (US); Alvin Cecil Fults, Amarillo, TX (US)

(73) Assignee: FEVERTAGS, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/993,390

(22) Filed: Aug. 14, 2020

(65) Prior Publication Data

US 2020/0367759 A1    Nov. 26, 2020

Related U.S. Application Data (63) Continuation of application No. 16/439,518, filed on Jun. 12, 2019, now Pat. No. 10,813,558, which is a
(Continued)

(51) Int. Cl.
*A61B 5/01* (2006.01)
*A61B 5/00* (2006.01)
(Continued)

(52) U.S. Cl.
CPC ............... *A61B 5/01* (2013.01); *A01K 11/00* (2013.01); *A01K 11/001* (2013.01);
(Continued)

(58) Field of Classification Search
CPC ....... A61B 5/01; A61B 5/6816; A61B 5/6817; A61B 5/0008; A61B 5/0022;
(Continued)

(56) References Cited

U.S. PATENT DOCUMENTS

| 3,781,837 A | 12/1973 | Anderson et al. |
| 4,865,044 A | 9/1989 | Wallace et al. |

(Continued)

FOREIGN PATENT DOCUMENTS

| KR | 20200060000192 U | 12/2006 |
| KR | 101213252 B1 | 12/2012 |
| KR | 1020180112972 A | 10/2018 |

OTHER PUBLICATIONS

Filing Receipt and Specification of U.S. Appl. No. 14/879,407, filed Oct. 9, 2015, titled Livestock Health Monitoring System and Method of Use, 21 pages.
(Continued)

*Primary Examiner* — Mohammad K Islam
(74) *Attorney, Agent, or Firm* — Jerry C. Harris, Jr.

(57) ABSTRACT

An animal wellness notification system includes an attachment body configured to securely engage with an ear of the animal; an elongated temperature probe secured to the attachment body and configured to extend within the ear of the animal; a housing secured to the attachment body; a computer disposed within the housing and operably associated with the temperature probe; and a notification device in data communication with the computer, the notification device being configured to provide notice if a temperature of the animal goes beyond a determined threshold.

22 Claims, 7 Drawing Sheets

Related U.S. Application Data continuation of application No. 15/440,793, filed on Feb. 23, 2017, now Pat. No. 10,398,317, and a continuation-in-part of application No. 14/879,407, filed on Oct. 9, 2015, now Pat. No. 10,687,515, and a continuation of application No. 16/872,617, filed on May 12, 2020, which is a continuation of application No. 14/879,407, filed on Oct. 9, 2015, now Pat. No. 10,687,515.

(60) Provisional application No. 62/337,400, filed on May 17, 2016, provisional application No. 62/102,416, filed on Jan. 12, 2015.

(51) Int. Cl.

| | | |
|---|---|---|
| *A01K 29/00* | (2006.01) | |
| *A01K 11/00* | (2006.01) | |
| *G01K 3/00* | (2006.01) | |
| *G01K 1/024* | (2021.01) | |
| *G08B 21/18* | (2006.01) | |
| *G01K 13/20* | (2021.01) | |

(52) U.S. Cl.
CPC .......... *A01K 11/004* (2013.01); *A01K 29/005* (2013.01); *A61B 5/0008* (2013.01); *A61B 5/0022* (2013.01); *A61B 5/6816* (2013.01); *A61B 5/6817* (2013.01); *A61B 5/742* (2013.01); *A61B 5/7405* (2013.01); *G01K 1/024* (2013.01); *G01K 3/005* (2013.01); *G01K 13/20* (2021.01); *G08B 21/182* (2013.01); *A61B 2503/40* (2013.01)

(58) Field of Classification Search
CPC ... A61B 5/7405; A61B 5/742; A61B 2503/40; A61B 5/746; A01K 11/001; A01K 11/004; A01K 11/00; G01K 1/024; G01K 3/005; G01K 13/002; G08B 21/182
See application file for complete search history.

(56) References Cited

U.S. PATENT DOCUMENTS

| | | | | |
|---|---|---|---|---|
| 5,725,308 | A * | 3/1998 | Smith | G01K 7/42 374/169 |
| 5,984,875 | A | 11/1999 | Brune | |
| 6,485,433 | B1 | 11/2002 | Peng | |
| 8,308,353 | B2 | 11/2012 | Yamaguchi | |
| 9,370,170 | B2 * | 6/2016 | Downing | A01K 11/006 |
| 9,504,387 | B2 * | 11/2016 | Alonsoperez Lanza | G06F 19/00 |
| 9,848,577 | B1 * | 12/2017 | Brandao | A61D 13/00 |
| 10,039,267 | B1 | 8/2018 | Thiex et al. | |
| 2002/0010390 | A1 | 1/2002 | Guice et al. | |
| 2002/0035340 | A1 | 3/2002 | Fraden et al. | |
| 2002/0154015 | A1 | 10/2002 | Hixson | |
| 2004/0233971 | A1 * | 11/2004 | Meads | G01K 1/026 374/208 |
| 2005/0059870 | A1 | 3/2005 | Aceti | |
| 2007/0135717 | A1 | 6/2007 | Uenishi et al. | |
| 2007/0143060 | A1 | 6/2007 | Chiu | |
| 2008/0312511 | A1 | 12/2008 | Osler et al. | |
| 2009/0312667 | A1 | 12/2009 | Utsunomiya et al. | |
| 2010/0160809 | A1 | 6/2010 | Laurence et al. | |
| 2010/0217099 | A1 | 8/2010 | LeBoeuf et al. | |
| 2011/0251514 | A1 | 10/2011 | Fults et al. | |
| 2013/0010997 | A1 | 1/2013 | Tanaka et al. | |
| 2013/0296685 | A1 | 11/2013 | Tsuboi et al. | |
| 2014/0333439 | A1 * | 11/2014 | Downing | G01K 13/223 340/573.3 |
| 2015/0039239 | A1 | 2/2015 | Shuler et al. | |
| 2015/0088028 | A1 | 3/2015 | Ledoux | |
| 2015/0334990 | A1 * | 11/2015 | Nir | A61B 5/024 600/301 |
| 2016/0073968 | A1 * | 3/2016 | Koyama | A61B 5/0537 600/301 |
| 2016/0165851 | A1 * | 6/2016 | Harty | A61D 17/002 600/595 |
| 2018/0235184 | A1 | 8/2018 | Harty et al. | |

OTHER PUBLICATIONS

Filing Receipt and Specification of U.S. Appl. No. 62/337,400, filed May 17, 2016, titled Livestock Health Monitoring System and Method of Use, 23 pages.

USPTO, International Search Report issued in PCT/US2017/019464, dated May 30, 2017, 2 pages.

USPTO, International Written Opinion issued in PCT/US2017/019464, dated Apr. 9, 2017, 5 pages.

Korean Patent Office, International Search Report issued in PCT/US2020/046776, dated Nov. 27, 2020, 3 pages.

Korean Patent Office, Written Opinion issued in PCT/US2020/046776, dated Nov. 25, 2020, 7 pages.

* cited by examiner

LIVESTOCK HEALTH MONITORING SYSTEM AND METHOD OF USE

CROSS-REFERENCE TO RELATED APPLICATIONS

This application is a continuation of, and claims priority to, U.S. patent application Ser. No. 16/439,518 filed on Jun. 12, 2019 and entitled "Livestock Health Monitoring System and Method of Use," which is a continuation of, and claims priority to, U.S. patent application Ser. No. 15/440,793 filed on Feb. 23, 2017 and entitled "Livestock Health Monitoring System and Method of Use," which claims priority to U.S. Provisional Patent Application Ser. No. 62/337,400 filed on May 17, 2016 and entitled "Livestock Health Monitoring System and Method of Use"; U.S. patent application Ser. No. 15/440,793 is also a continuation-in-part of U.S. patent application Ser. No. 14/879,407 filed on Oct. 9, 2015 and entitled "Livestock Health Monitoring System Having Elongated Temperature Probe for the Ear and Method of Use," which claims priority to U.S. Provisional Patent Application Ser. No. 62/102,416 filed on Jan. 12, 2015 and entitled "Electrical Mechanical Device Used to Detect and Alarm Health Status of Bovine"; this application is also a continuation of, and claims priority to, U.S. patent application Ser. No. 16/872,617, filed May 12, 2020 and entitled "Livestock Health Monitoring System and Method of Use" which is a continuation of, and claims priority to U.S. patent application Ser. No. 14/879,407, filed on Oct. 9, 2015 and entitled "Livestock Health Monitoring System Having Elongated Temperature Probe for the Ear and Method of Use", which claims priority to U.S. Provisional Patent Application No. 62/102,416 filed Jan. 12, 2015 and entitled "Electrical Mechanical Device Used to Detect and Alarm Health Status of Bovine."

BACKGROUND

Field of the Invention

The present invention relates generally to systems and methods to determine the health of livestock, and more specifically, to a livestock health monitoring system for data collection and detection of abnormal health conditions.

Description of Related Art

Figure 1:
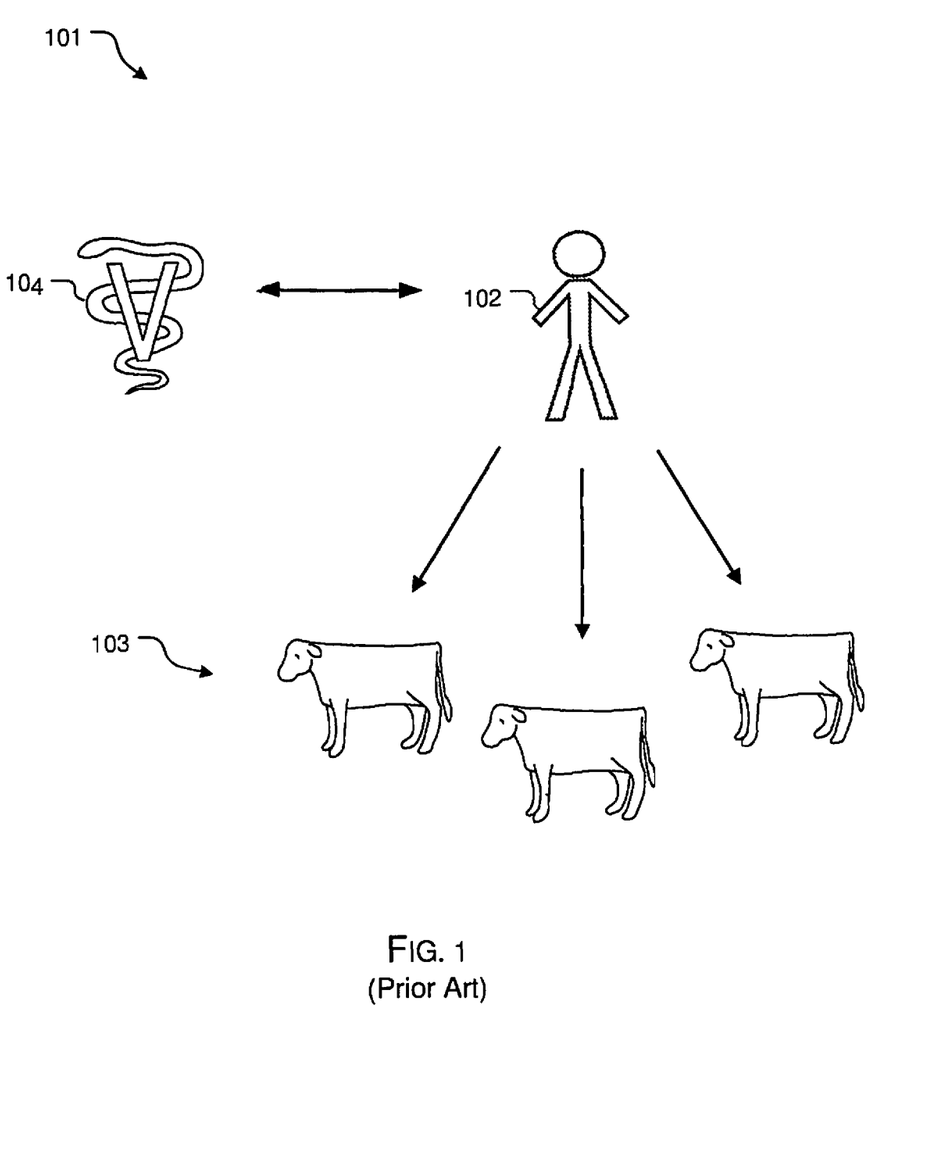
FIG. 1 is a simplified schematic of a common livestock method to determine wellness of the livestock.
Figure 2:
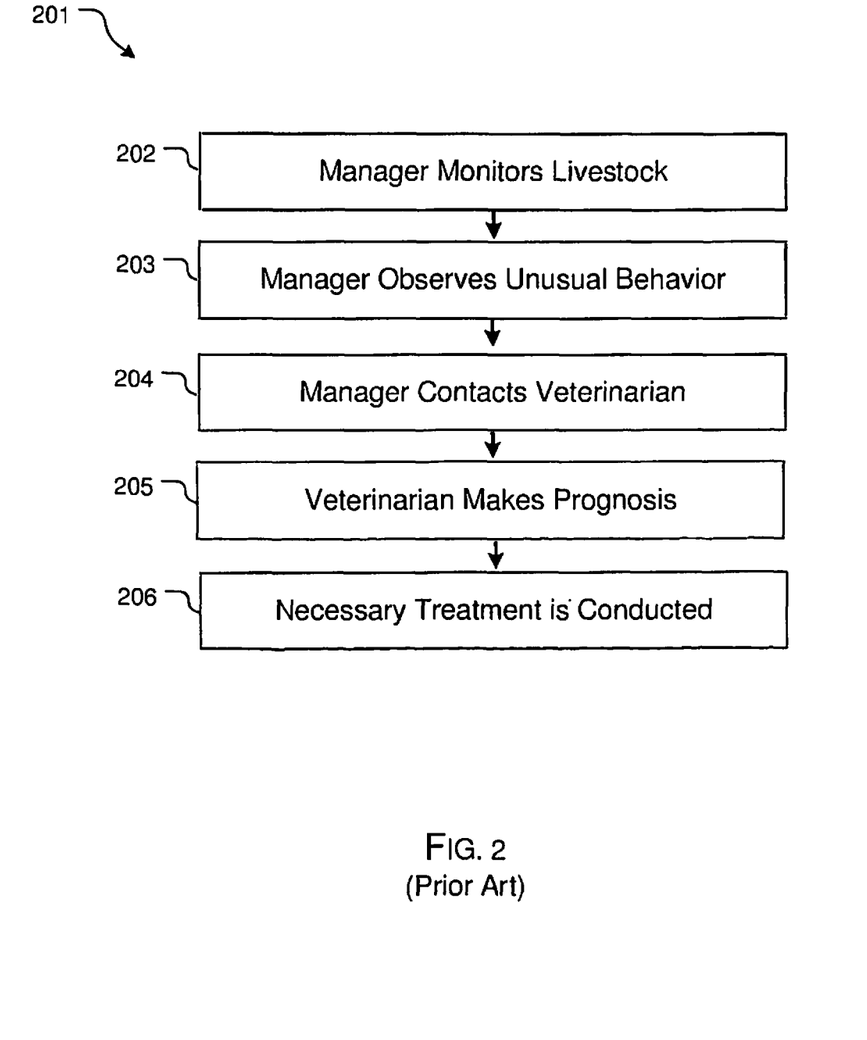
FIG. 2 is a flowchart of a process of the simplified schematic of FIG. 1.

Systems and methods to determine the health of livestock are well known in the art and are effective means to detect illness and implement treatment in livestock. For example, FIG. 1 depicts a simplified schematic of a conventional livestock monitoring system 101 having a livestock manager 102 overseeing a plurality of livestock 103 and in communication with a veterinarian 104. As shown in FIG. 2, a flowchart 201 depicts an example of the process of system 101. The livestock manager 102 monitors livestock 103 via visual inspection. When unusual behavior of the livestock occurs, as indicative of illness, the livestock manager 102 contacts a veterinarian 104, who then makes a prognosis and begins treatment accordingly, as shown with boxes 203-206.

One of the problems commonly associated with system 101 is insufficient monitoring and/or inexperience of the livestock manager. For example, the process of monitoring could involve a large number of livestock, making the monitoring process difficult. In addition, the process suffers a substantial risk of human error, as many livestock illnesses are visually undetectable and/or the livestock manager fails to adequately determine whether the livestock is ill.

Accordingly, although great strides have been made in the area of system and methods to determine livestock wellness, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional livestock monitoring systems. Specifically, the present invention provides a rapid and effective means to monitor large numbers of livestock and reduces the risk of human error. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 3:
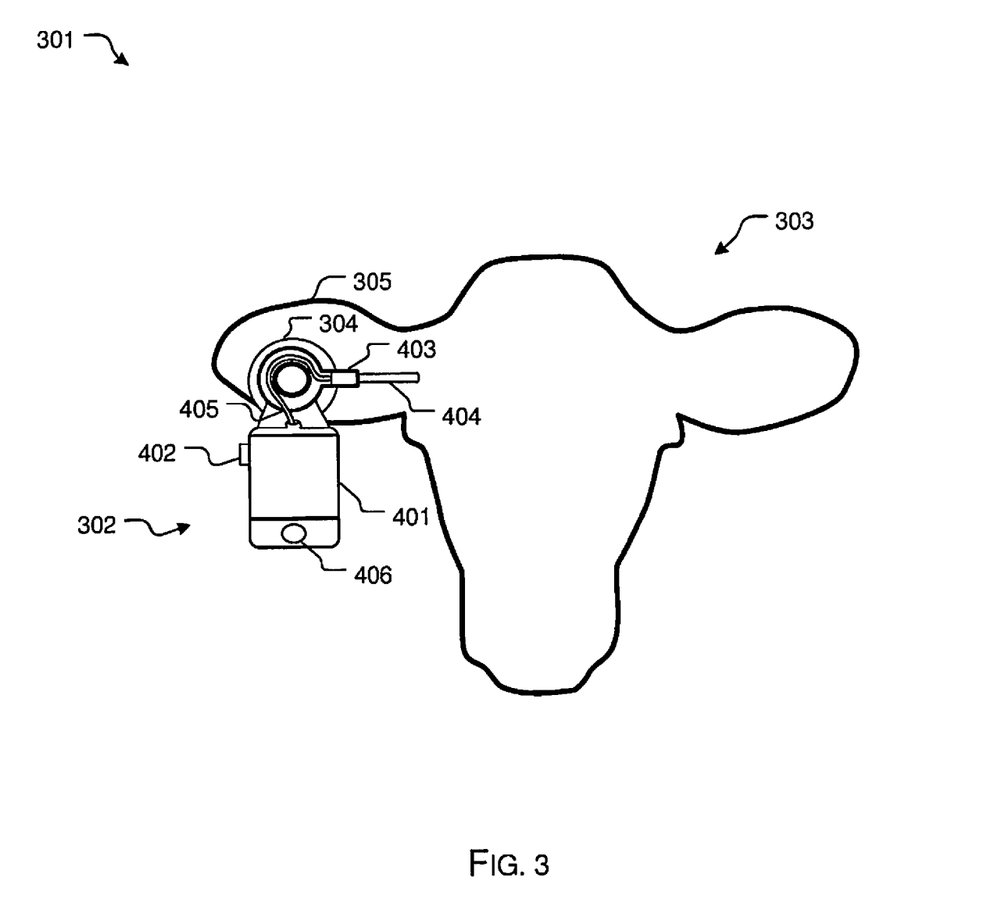
FIG. 3 is a front view of a livestock health monitoring system in accordance with a preferred embodiment of the present application.

Referring now to the drawings wherein like reference characters identify corresponding or similar elements throughout the several views, FIG. 3 depicts a front view of a livestock health monitoring system 301 in accordance with a preferred embodiment of the present application. It will be appreciated that system 301 overcomes one or more of the above-listed problems commonly associated with conventional systems and method to monitor livestock wellness.

In the contemplated embodiment, system 301 includes a health monitoring device 302 in communication with an animal 303 via an ear attachment 304. During use, the ear attachment 304 is secured to the ear of the animal (not shown) via one or more types of fasteners commonly known in the art. To achieve this feature, ear attachment 304 includes a body having a hole 701 extending there through. The fastener is secured to the hole 701, which in turn is secured to the ear.

Figure 4:
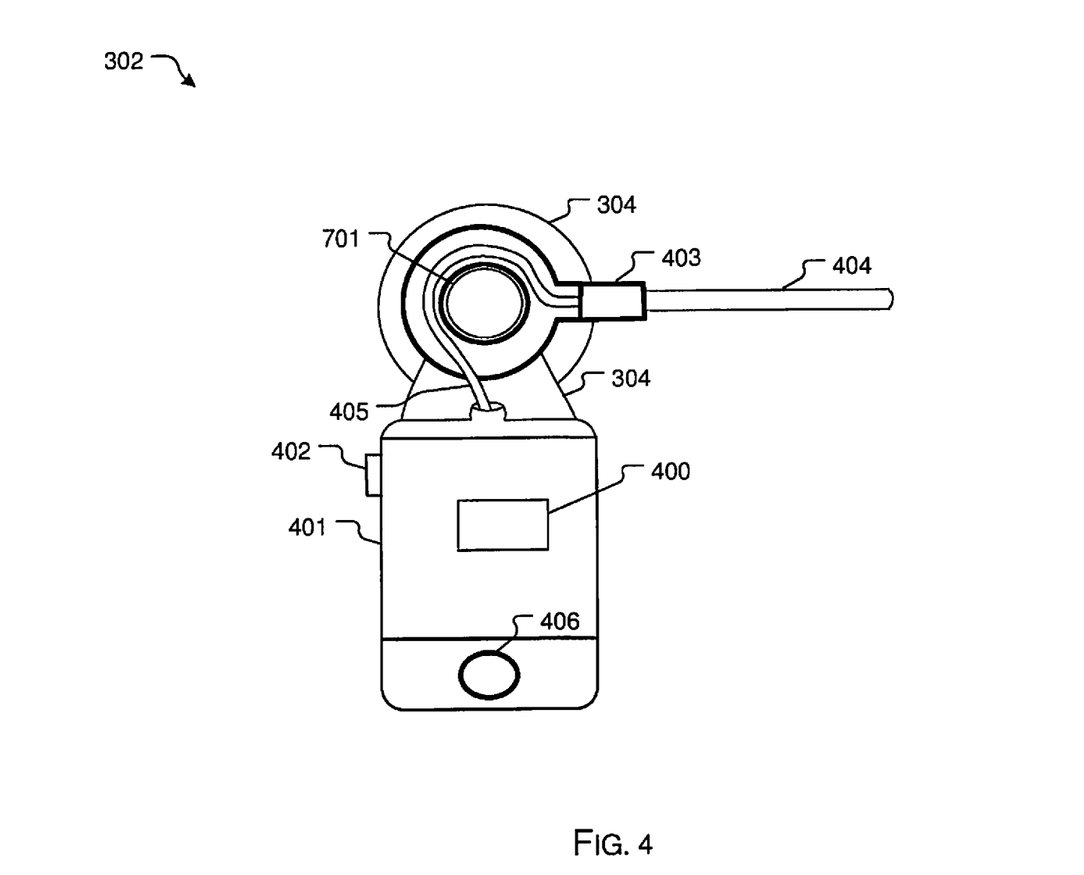
FIG. 4 is a front view of the heath monitoring device from FIG. 3.
Figure 6:
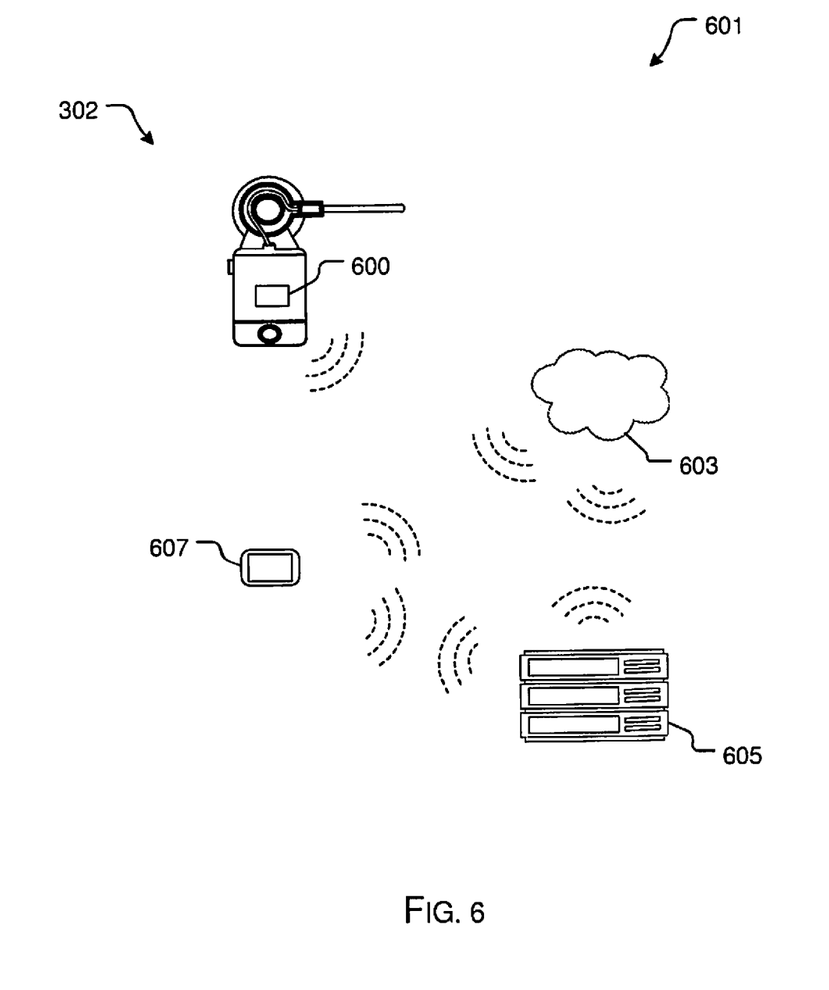
FIG. 6 is a simplified schematic of a system in accordance with an alternative embodiment of the present application.

As shown in FIG. 4, the health monitoring device 302 comprises of one or more of a data collection house 401, an on/off depression switch 402, in communication with an ear attachment 304 via a rotational device 403 and a temperature probe 404 via a wire 405. In the preferred embodiment, the elongated temperature probe 404 is positioned through the rotation device 403 and comprises a material capable of changing hardness upon reaching a particular temperature. In addition, the data collection house 401 can comprise a notification device 406 and is enclosed in weather resistant plastic. In the preferred embodiment, the notification device 406 is a light that can be visually seen by the worker; however, it will be appreciated that the notification device 406 could be an audible speaker and/or a transmitter configured to provide notification to a remote computer, as depicted in FIG. 6.

A computer system 400 having the necessary software, hardware, and power supply are carried within housing 401 to determine if a temperature threshold is reached and to activate device 406.

Figure 5:
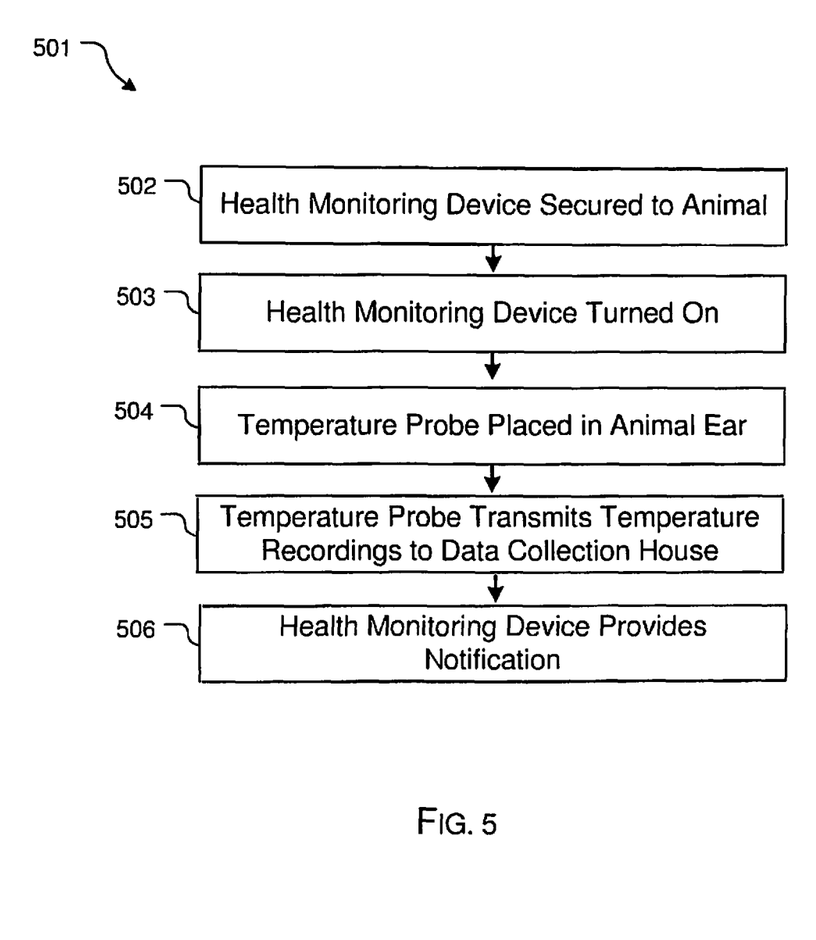
FIG. 5 is a flowchart of the process of FIG. 3.

In FIG. 5, a flowchart 501 depicts a preferred process of system 301. The heath monitoring device 302 is secured to the animal's ear 305 via the ear attachment 304 and turned on by the on/off depression switch 402, as shown with boxes 502 and 503. A temperature probe 404 of the appropriate length is placed in communication with the ear 305 and transmits temperature recordings to the data collection house 401 via the wire 405, as shown with boxes 504 and 505. The health monitoring device 302 monitors the animal's body temperature and can provide a notification when user set parameters are breached, as shown with box 506.

It should be understood that body temperature measurements in livestock can indicate useful information in regards to illnesses, disease, distress, and hormone levels.

It should be appreciated that one of the unique features believed characteristic of the present application is the incorporation of an on/off depression switch 402. It is understood that this switch will reduce the risk of the animal deactivating the health monitoring device. During use, the worker can determine whether the system is active by depressing the switch 402.

Additional unique features believed characteristic of the present application are the rotational feature 403 of the health monitoring device 302 and the material of the temperature probe, capable of changing hardness. It is understood that these features allows for stabilization and comfort of the temperature probe 404 in the animal ear 305.

In one embodiment, it is contemplated that the health monitoring device 302 can function independently by way of the notification light 406 when a user set parameter is breached. For example, if the animal's temperature increases to a certain value, as set by the user, the notification light 406 will signal to the user that such a parameter has been met. It is understood that this feature will allow for quick visual identification of ill livestock.

Accordingly, as shown in FIGS. 3-5, a notification system is disclosed herein wherein a temperature probe is secured within the ear of the animal and provides notification, preferably via a light, when a threshold temperature reading is reached. Thus, the system is configured to provide notification when the animal falls outside a determined temperature range. The notification could be via a light, audible noise, and/or a wireless transmission, as discussed in the below disclosure.

Referring now to FIG. 6, a simplified schematic of a system 601 is shown in accordance with an alternative embodiment of the present application. System 601 incorporates the features of the system 301, and is further provided with a transmission system 600 having a transmitter configured to communication wirelessly to a cloud service 603 and/or database 605 and/or a portable computer such as a phone, tablet, or personal computer.

During use, system 601 allows the monitoring of multiple animals simultaneously and reduces the chances of human error. For example, the computer 607 could provide notification when system 301 is triggered, which in turn allows the worker to conduct visual inspection of the animal.

Figure 7:
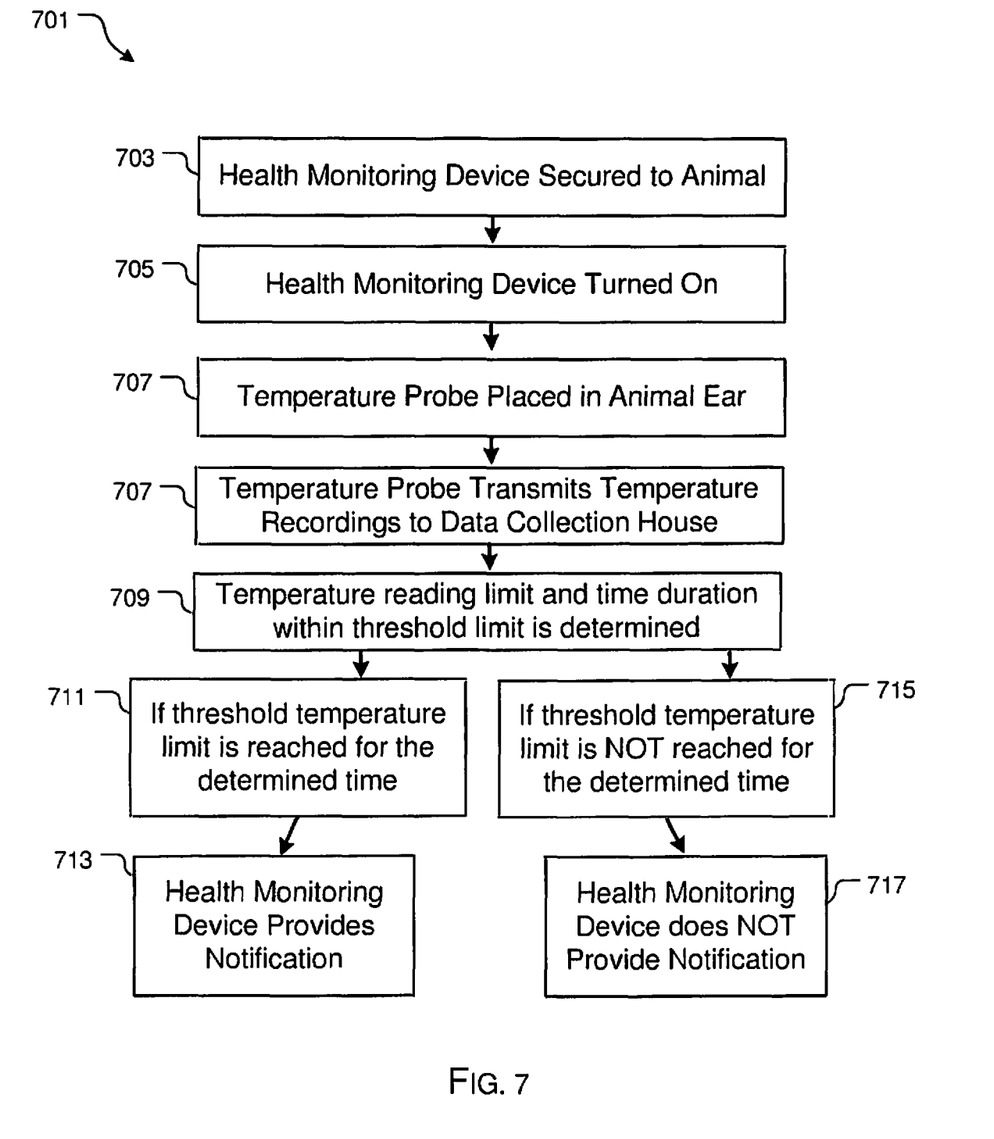
FIG. 7 is a flow chart depicting the preferred method of use.

Referring now to FIG. 7, a flowchart 701 depicting the preferred method of use is shown. The process includes activating a health monitoring device and placing a probe of the health monitoring device within the ear of the animal, as depicted in boxes 703-707. This feature can be achieved via one or more of the devices discussed above. The temperature measured by the probe is then transmitted to a data collection house via one or more transmitters, as shown in box 707.

One the unique features of the preferred method is selecting a temperature threshold along with a time duration that the animal reaches and/or exceed the temperature threshold, as shown in box 709. One or more computers are utilized to record and determine whether the animal's temperature remains above the threshold for the selected duration of time. If so, the health monitoring device provides notice in the form of a visual or audible alert, as shown in boxes 711, 713. Further, one or more computers monitoring the animals could provide visual or audible notification via a display. In the alternative, if the threshold temperature does not last the selected duration of time, the temperature readings are recorded but the health monitoring device is not provide an alert.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An animal wellness notification system, comprising:
    an attachment body configured to engage with an ear of the animal;
    a temperature monitor;
    a housing secured to the attachment body;
    a computer disposed within the housing; and
    a notification device in data communication with the computer, wherein the notification device is configured to provide notice, and wherein the computer is configured to:
        receive a selection of a temperature range along with a time duration;
        record an animal's temperature for the selected time duration;
        determine whether the animal's temperature remains outside the temperature range for the time duration; and
        cause the notification device to provide the notice, after the time duration, if the animal's temperature remained outside the temperature range for the time duration.

2. The system of claim 1, wherein the temperature range is a temperature threshold.

3. The system of claim 1, further comprising a switch secured to the housing and operably associated with computer.

4. The system of claim 1, wherein the notification device is a light.

5. The system of claim 1, wherein the notification device is a speaker.

6. The system of claim 1, the notification device having a transmitter configured to wirelessly communicate with a portable computer.

7. The system of claim 6, further comprising:
    a database in communication with the computer, wherein the database is configured to store data from the notification device.

8. An animal wellness notification system, comprising:
    a temperature monitor configured to generate temperature data;
    a computer configured to process the temperature data; and
    a notification device, wherein the animal wellness notification system is configured to:
        receive a selection of a temperature range along with a time duration;
        record an animal's temperature for the selected time duration;
        determine whether the animal's temperature remains outside the temperature range for the time duration; and
        cause the notification device to provide notice, after the selected time duration, if the temperature data indicates that the animal's temperature remained outside the temperature range for the selected time duration.

9. The system of claim 8, further comprising:
    an attachment body configured to engage with the ear of the animal, wherein
    the temperature monitor is secured to the attachment body.

10. The system of claim 9, further comprising a housing secured to the attachment body.

11. The system of claim 10, wherein the computer is disposed within the housing and operably associated with the temperature monitor.

12. The system of claim 11, wherein the computer is configured to determine if the temperature data indicates that the animal's temperature remained outside the selected temperature range for the selected time duration.

13. The system of claim 8, wherein the notification device is a light.

14. The system of claim 8, wherein the notification device is a speaker.

15. The system of claim 8, wherein the temperature range is a temperature threshold.

16. The system of claim 8, further comprising:
    a transmitter configured to wirelessly communicate the temperature data with the computer, wherein the computer is a remote computer and the remote computer is configured to determine if the temperature data indicates that the animal's temperature remained outside the selected temperature range for the selected time duration.

17. The system of claim 16, further comprising:
    an attachment body configured to engage with the ear of the animal, wherein
    the temperature monitor is secured to the attachment body.

18. The system of claim 17, further comprising a housing secured to the attachment body.

19. The system of claim 16, wherein the notification device is a light.

20. The system of claim 16, wherein the notification device is a speaker.

21. The system of claim 16, wherein the temperature range is a temperature threshold.

22. The system of claim 16, further comprising:
    a database in communication with the remote computer, wherein the database is configured to store data from the transmitter.

* * * * *